(12) United States Patent
Wang et al.

(10) Patent No.: US 8,596,859 B2
(45) Date of Patent: Dec. 3, 2013

(54) DEVICE AND SYSTEM FOR MIXING AND DISPENSING COMPONENTS STORED SEPARATELY FROM ONE ANOTHER

(75) Inventors: Yiping Wang, Howell, NJ (US);
William S. Wei, Belle Meade, NJ (US);
Daniel W. Frank, Broomall, PA (US)

(73) Assignee: Nexmed Holdings, Inc., San Diego, CA (US)

( * ) Notice: Subject to any disclaimer, the term of this patent is extended or adjusted under 35 U.S.C. 154(b) by 605 days.

(21) Appl. No.: 12/734,404

(22) PCT Filed: Nov. 6, 2008

(86) PCT No.: PCT/US2008/012591
§ 371 (c)(1),
(2), (4) Date: Apr. 29, 2010

(87) PCT Pub. No.: WO2009/061480
PCT Pub. Date: May 14, 2009

(65) Prior Publication Data
US 2010/0260004 A1    Oct. 14, 2010

Related U.S. Application Data

(60) Provisional application No. 61/002,391, filed on Nov. 8, 2007.

(51) Int. Cl.
*B01F 5/08* (2006.01)
(52) U.S. Cl.
USPC ........................................ 366/176.3; 366/267
(58) Field of Classification Search
USPC ................ 366/130, 176.3, 267, 268
See application file for complete search history.

(56) References Cited

U.S. PATENT DOCUMENTS 2,084,156 A * 6/1937 Marsden .................... 366/176.3
2,477,598 A * 8/1949 Hain ............................. 366/334
(Continued)

FOREIGN PATENT DOCUMENTS

EP    1504728 A1    2/2005
IE     914563 A1    7/1992
(Continued)

OTHER PUBLICATIONS

International Search Report and Written Opinion issued in PCT/US2008/12591 dated Jan. 8, 2009.
(Continued)

*Primary Examiner* — David Sorkin
(74) *Attorney, Agent, or Firm* — Foley & Lardner LLP

(57) ABSTRACT

Mixing devices and systems are disclosed for storing separate components and for mixing and dispensing those components on demand. A mixing device includes a syringe having a generally tubular housing formed with a mixing chamber. A plunger is fitted to the tubular housing to form a first syringe. A dispensing syringe is releasably connected to the mixing chamber. At this point each syringe holds a desired amount of a mixture component. The contents of one syringe are passed through the mixing chamber to the other syringe, forming a usually incomplete mixture. The mixture is then passed through the mixing chamber to the other syringe. Multiple passes through the mixing chamber are continued until the desired mixing result is achieved, and the mixture material is contained in the second syringe that is used to thereafter dispense desired amounts of the mixture.

6 Claims, 2 Drawing Sheets

(56) References Cited

U.S. PATENT DOCUMENTS

| | | | |
|---|---|---|---|
| 3,010,705 A * | 11/1961 | Brown | 366/268 |
| 3,546,129 A | 12/1970 | Berg et al. | |
| 3,700,215 A * | 10/1972 | Hardman et al. | 366/268 |
| 3,860,218 A * | 1/1975 | Hurlimann | 366/268 |
| 4,968,299 A | 11/1990 | Ahlstrand et al. | |
| 5,033,650 A | 7/1991 | Colin et al. | |
| 5,425,580 A * | 6/1995 | Beller | 366/131 |
| 6,062,722 A * | 5/2000 | Lake | 366/130 |
| 6,305,413 B1 * | 10/2001 | Fischer et al. | 137/493.8 |
| 8,109,902 B2 * | 2/2012 | Middleton et al. | 604/82 |
| 2007/0104651 A1 | 5/2007 | Wright | |

FOREIGN PATENT DOCUMENTS

| | | |
|---|---|---|
| JP | 2005186026 A | 7/2005 |
| WO | 9211928 A1 | 7/1992 |
| WO | 2005089500 A2 | 9/2005 |

OTHER PUBLICATIONS

First Exam Report and Written Opinion issued by the Australian Patent Office in 2008325087 dated Dec. 14, 2012.

Office Action issued by the Mexican Institute of Industrial Property in MX/a/2010/005146 dated Mar. 6, 2013.

Office Action issued by the Japanese Patent Office in 2010-533108 dated Mar. 22, 2013.

* cited by examiner

DEVICE AND SYSTEM FOR MIXING AND DISPENSING COMPONENTS STORED SEPARATELY FROM ONE ANOTHER

The present application is the National Stage of International Application No. PCT/US2008/012591, filed Nov. 6, 2008, which claims the benefit of U.S. Ser. No. 61/002,391, filed Nov. 8, 2007; the contents of all the preceding patent applications are incorporated by reference herein in their entireties, including drawings.

FIELD OF THE INVENTION

This invention relates generally to a mixing device including a container, such as a syringe, having an integral mixing chamber, such as a chamber with one or more emulsifying passageways, and provision for connection to a separate container. The invention also relates to a system including the mixing device, a disposable dispensing container for dispensing a medicament to a targeted site, optionally including a unit dose dial for metering a quantity of a unit dose to be dispensed from a multiple-dose medicament container, and a support base for the dispensing container.

BACKGROUND OF THE INVENTION

Certain medicaments and other materials are comprised of components that are incompatible with one another as a previously prepared mixture, and accordingly, must be mixed just prior to dispensing. For example, emulsifying needles have been provided with a single tubular passageway with a socket at each end for connection between a pair of syringes carrying the separate components. One example of incompatible components includes, for example, an oil and an aqueous solution prepared on demand to form an emulsion having a relatively short shelf life at room temperature. The components may be considered to be "incompatible" with one another for a variety of reasons. For example, certain emulsified mixtures used in the health care field become unstable upon mixing, with the resulting mixture having a limited shelf life not suitable for storage, or for practical, commercial distribution. Instability may arise due to chemical reactions as well as interactions that do not involve chemical bonds. Accordingly, practical applications of such materials require devices and systems to prepare mixtures of components which must be stored separately until the time of application or use, or stored at a relatively lower temperature, for example by refrigeration, prior to use.

Emulsifying needles have been proposed for mixing two components (e.g. oil and water or other aqueous solution) carried in their own respective general purpose syringes. Typically, the contents of one syringe are passed through the emulsifying needle to the other syringe to contact its contents. The receiving syringe is then pumped to move the components in a reverse direction through the emulsifying needle to the now empty syringe. Successive iterations of the pumping operations are carried out until the desired mixture condition is reached. For example, one common mixture condition is the emulsification of the two components. Other types of mixtures other than emulsifications may be prepared in a similar manner. Mixing arrangements employing an emulsification needle and general purpose syringes may be unsuitable for certain applications, as where a disposable mixing device is preferred.

As will be appreciated by those skilled in the art, the components frequently have substantially different viscosities and other physical properties either in their separate stored state or when combined in a mixture, so as to require substantial pressures to be developed by the syringes, when passing the mixtures back and forth through the emulsifying needle. In the presence of elevated pressures, the emulsifying needle may become dislodged from one or both syringes, unintentionally, thereby compromising the preparation process.

Prior art arrangements suffer from another disadvantage in that the emulsifying needles, in order to reduce costs, include separable connectors for joinder to common, general purpose syringes. Thus, the arrangement does not provide a control to restrict the syringes which can be used in the process.

As a further drawback, the emulsifying needles require a fairly expensive construction since they utilize surgical stainless steel materials processed according to familiar standards required in the medical industry. The emulsifying needles present a substantial capital investment and hence are adapted for re-use, requiring an intervening cleaning and sterilization procedure, at a minimum. This accordingly presents questions of cross contamination or other questionable conditions, adding to the complexity of the work environment.

As an another drawback, the single emulsifying passageway (or single passage) emulsifying needles in the art require many iterative back and forth passes to achieve uniform mixing, especially for higher viscosity medicaments such as gels. This drawback may cause potential non-uniform multiple-dose medicament. Non-uniform multiple-dose medicament may pose risk to patients either by under- or over-dose.

SUMMARY OF THE INVENTION

The present invention provides a novel and improved mixing device and system in which a syringe is provided with a generally tubular housing having opposed proximal and distal end portions. The distal end portion terminates in a mixing chamber such as a unitary nozzle defining one or more emulsifying passageways. Also included is a plunger configured for axial movement within the tubular housing.

In one example, a system is provided in which the nozzle is adapted to interlock with a second container such as a dispensing syringe or a pump like device, so as to receive a component such as a liquid infusion carried in the second syringe. The components of the syringes are passed through the mixing chamber, alternately from one syringe to the other, to provide a mixture of a desired condition, such as an emulsification of the two components.

In one example, the mixing device is comprised of a unitary molded body defining a tubular housing and mixing chamber. Thus the mixing device can be commercially provided in an economical manner, using only two components including the plastic molding containing the tubular housing and mixing chamber and a plunger configured to fit within the tubular housing for reciprocal axial movement therewithin. Further, the mixing device can be pre-filled to provide convenient storage of a first component.

Numerous other advantages and features of the present invention will become readily apparent from the following detailed description and from the accompanying drawings.

DESCRIPTION OF PREFERRED EMBODIMENTS

Figure 1:
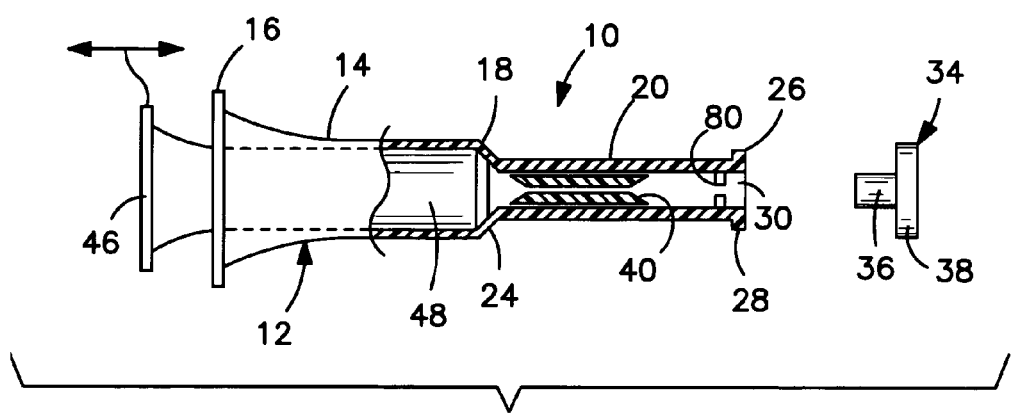
FIG. 1 is a schematic elevational view, shown partly in cross section, of a mixing device illustrating the present invention.

The invention disclosed herein is, of course, susceptible of embodiment in many different forms. Shown in the drawings and described herein below in detail are the preferred embodiments of the invention. It is to be understood, however, that the present disclosure is an exemplification of the principles of the invention and does not limit the invention to the illustrated embodiments.

For ease of description, mixing devices and systems embodying the present invention are described herein below in their usual assembled position as shown in the accompanying drawings and terms such as proximal and distal, front, rear, upper, lower, horizontal, longitudinal, etc. may be used herein with reference to this usual position. However, the mixing devices and systems may be manufactured, transported, sold, or used in orientations other than that described and shown herein.

Referring now to the drawings, and initially to FIG. 1, a mixing device is generally indicated at 10. Included is a body generally indicated at 12 which is preferably made of one-piece integral construction utilizing molding or other fabrication techniques. Preferably, body 12 is made of a rigid plastic material, clear, translucent or opaque, such as polyolefin, including polyethylene, polypropylene, and the like, suitable for injection molding.

Preferably, body 12 is hollow, or at least partially hollow throughout its entire length. Body 12 includes a hollow generally tubular housing 14 having proximal end portion 16 and a distal end portion 18. Body 12 further includes a unitary or integral mixing chamber 20 at the distal end 18 of tubular housing 14 and connected thereto by an optional frustoconical transition 24. Mixing chamber 20 has a nozzle or open free end 26, preferably fitted with an outwardly extending flange 28, disposed about an opening 30. A separate closure 34 includes a plug-like body 36 that is dimensioned so as to be received within opening 30, and an enlarged head 38 to facilitate its withdrawal from the open end of body 12, once fitted thereto so as to seal open end 30.

In a preferred embodiment, mixing chamber 20 is adapted to emulsify components that are passed through the mixing chamber. Accordingly, one or more interior channels are formed in the mixing chamber. In a particularly preferred embodiment illustrated in FIG. 1, an internal structure 40 is disposed within the hollow interior of mixing chamber 20 having multiple passageways. As can be seen in FIG. 1, the opposed ends of interior structure 40 are flared in an inwardly extending or concave frustoconical shape. Also, as shown in FIG. 1, interior structure 40 is located adjacent the tubular housing 14 and is spaced from the open end 30. Interior structure 40 preferably cooperates with the mixing chamber walls to define multiple flow passageways. Most preferably, the mixing chamber cooperates to emulsify the components. Accordingly, the structure 40 is dimensioned so as to cooperate with the walls of the mixing chamber 20 to form a high shear flow for efficient emulsification of components with a minimum number of iterations as the contained contents are combined with an aqueous vehicle, or the like, and pumped back and forth through the mixing chamber. The present invention also contemplates mixing to achieve results other than emulsification, and accordingly, a wide variety of interior structures, e.g., static mixers, or arrangements with no intermediate interior structure, are contemplated as well by the present invention.

The present mixing chambers can be of virtually any length, internal dimensions and constructions as may be desired. The present mixing chamber be provided with one or more interior dividing members or partitions defining one or more mixing channels of desirable length and cross sectional size within mixing chamber 20. Most preferably, the interior structure is integral with the mixing chamber housing and the remainder of body 12, but can be added during or after molding of body 12, if desired.

Mixing device 10 further includes a plunger 46 having a body portion 48, adapted to fit within tubular housing 14 in a known manner so as to cooperate with tubular housing 14 to function as a dispensing actuator for a syringe-like device. In the preferred embodiment, tubular housing 14 is employed to hold a desired amount of a first component for the mixture, such as water, an aqueous gel, or an aqueous or other liquid solution as may be desired to serve as a delivery vehicle for active ingredient or ingredients contained in a separate compartment. If desired, the plunger 46 may be withdrawn and temporarily removed from body 12, with the tubular housing 14 being filled with the first component, as desired. Alternatively, the open end 30 may be immersed in a supply of the first mixture component and plunger 46 withdrawn in a known manner so as to pull liquid into tubular housing 14, ready for a mixing event. If desired, a filling needle or the like can be fitted to the mixing device to withdraw material from conventional sterile containers, or the like.

Figure 2:
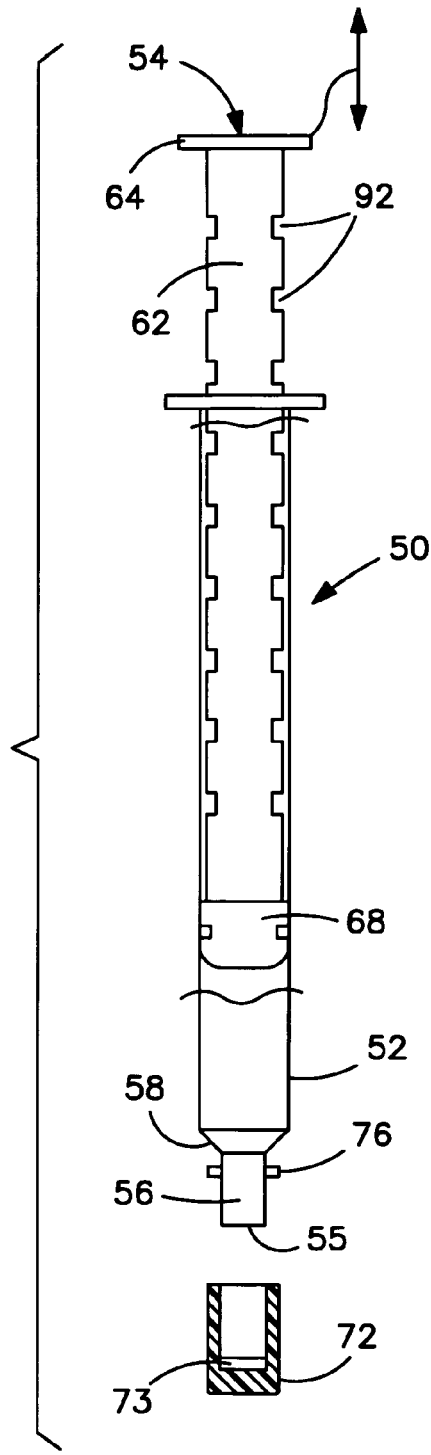
FIG. 2 is an elevational view, shown partly in cross section, of a dispensing syringe for use with the device of FIG. 1.

Turning now to FIG. 2, a dispensing syringe, containing one or more active ingredients in a suitable not aqueous carrier, is generally indicated at 50. Included is a tubular housing 52 having a hollow bore for receiving a plunger 54. Tubular housing 52 is preferably hollow throughout and terminates in a discharge nozzle portion 56 orifice 55 connected to tubular housing 52 through an optional transition member 58, usually having a frustoconical shape. The dispensing syringe 50 is preferably made in a manner similar to that of body 12, as discussed above.

Plunger 54 includes an elongated body 62 having an enlarged head 64 at one end that provides a convenient, manually graspable end portion, as is known. A seal such as piston 68 is carried at the free end of body 62 and is preferably of a material more resilient than body 62, so as to provide wiping engagement with the interior walls of tubular housing 52, as plunger 54 is reciprocated within the tubular housing and piston mover axially therewithin. If desired, seal piston 68 can be omitted in favor of a free end portion of body 62 forming a wiping or other sealing engagement with tubular housing 52.

That portion of the seal or piston that comes in contact with the contents of tubular housing 52 must be compatible therewith. To that end, seal or piston 68 can be provided with a fluorocarbon (e.g., Teflon®) coating, a silicone coating, or the like, or made from an inert material such as silicone rubber, and the like.

A second component to be added to form the mixture is preferably stored in the hollow interior of tubular housing 52. In the preferred embodiment, the material stored in tubular housing 52 has the form of an oil or a non-runny semi-solid material, such as an oil paste, ointment, gel, oil suspension, viscous solution, or colloidal suspension, salve, paste, or the like. In one instance, tubular housing 52 holds an oil paste with alprostadil, used to form VITAROS™ male erectile dysfunction treating formulations that are stable at room temperatures.

It may not be necessary in all instances to provide a resilient seal or piston 68 of the type described above however. Rather, an outwardly protruding ring of the same material as body 62 or a featureless plunger tip may be sufficient for some applications.

A separate closure in the form of a cap 72 is fitted over the generally cylindrical end portion 56 so as to occlude orifice 55 Cap 72 can be provided with a flexible liner 73, e.g., a fluorocarbon liner, that contacts and seals orifice 55 when in place. An engagement member 76 is provided on end portion 56 for mating with a complementary engagement member 80 formed adjacent the discharge opening 30 of mixing device 10. The cooperating engagement members 76, 80 may comprise, for example, a bayonet interlock, or a threaded engagement or other conventional interlocking arrangement as may be desired. The purpose of engagement members 76, 80 is to provide a releasable engagement between mixing device 10 and dispensing plunger 50 that is sufficient to withstand pressures generated during a mixing event, without requiring manual pressure to hold the members 10, 50, together.

As mentioned, the system comprising mixing device 10 and dispensing syringe or device 50 is provided to mix, on demand, two or more components unsuitable for pre-mixing and prolonged storage together. In a preferred embodiment, mixing device 10 is pre-filled and shipped with a desired quantity of an aqueous or other liquid component, while dispensing syringe or device 50 is pre-filled and shipped with a semi-solid flowable component, such as a paste material, stored in dispensing syringe 50. As mentioned, the liquid component may also be introduced into the mixing device just prior to the mixing event.

Preparations for the mixing event include removing the closures 34, 72 from mixing device 10 and dispensing device 50 and thereafter introducing end portion 56 of dispensing syringe 50 into orifice 30 of mixing device 10. The interlocking engagement members 76, 80 are thereafter configured so as to releasably hold the mixing device 10 and dispensing syringe 50 together in a "hands-off" free standing manner that does not require manual pressure. As indicated in the preferred embodiments of FIGS. 1 and 2, the orifice 54 of dispensing syringe 50 extends past engagement member 80 of mixing device 10 so as to be located generally proximal to interior structure 40.

One of the plungers 46, 54 is depressed so as to move its contents through mixing chamber 20 to contact the contents of the other container. For example, plunger 46 may be depressed so as to discharge the contents of mixing device 10 through mixing chamber 20, so as to enter the interior of dispensing syringe 50, to thereby mix with its contents. It is anticipated that the mixture may not be completed to the desired condition, e.g., emulsification. Accordingly, plunger 54 is then depressed so as to discharge the mixture back through mixing chamber 20 so as to enter the empty, or substantially empty, tubular housing 14 of mixing device 10. Thereafter, plunger 46 is depressed so as to again pass the mixture through mixing chamber 20. Successive iterations are carried out, as required to produce the desired end result. For example, when an emulsification is desired, successive iterations are carried out to pass the mixture a desired number of times through mixing chamber 20, and through the one or more emulsification passageways formed by the cooperation of interior structure 40 with the hollow tubular exterior of the mixing chamber. Upon attainment of the desired mixture condition, plunger 46 is depressed a final time, so as to move the mixture into the hollow interior of dispensing syringe 50.

The dispensing syringe is thereby filled with a recently produced mixture of the desired components. As mentioned above, two components are combined by mixing to form a mixture such as an emulsion. If desired, additional components may be added to the mixture by replacing the mixing device 10 or dispensing syringe 50 with a similar member containing an additional component. The mixing operation is then continued in the manner described above until the desired mixing condition is achieved, and the mixture is stored within dispensing syringe 50. The dispensing syringe is now available for dispensing a precisely controlled, desired quantity of mixture. For example, the dispensing syringe 50 may be employed to deliver a desired amount of medicament to a targeted site.

It will be appreciated by those skilled in the art that the dispensed amount of mixture from dispensing syringe 50 can be accurately controlled in a customary manner. If desired, a unit dose dial such as a stop collar 90 may be fitted to body 62 of plunger 54 so as to limit the travel of plunger 54 within tubular housing 52. In a preferred embodiment, body 62 of plunger 54 is provided with a series of recesses 92 so as to provide convenient selectable engagement with stop collar 90. If desired, the recesses 92 can be replaced with other conventional engagement features so as to retain stop collar 90 at a desired position along body 62. For example, recesses 92 could be replaced with a series of blind holes dimensioned so as to receive a resilient pin (not shown) disposed on the interior of stop collar 90.

Figure 3:
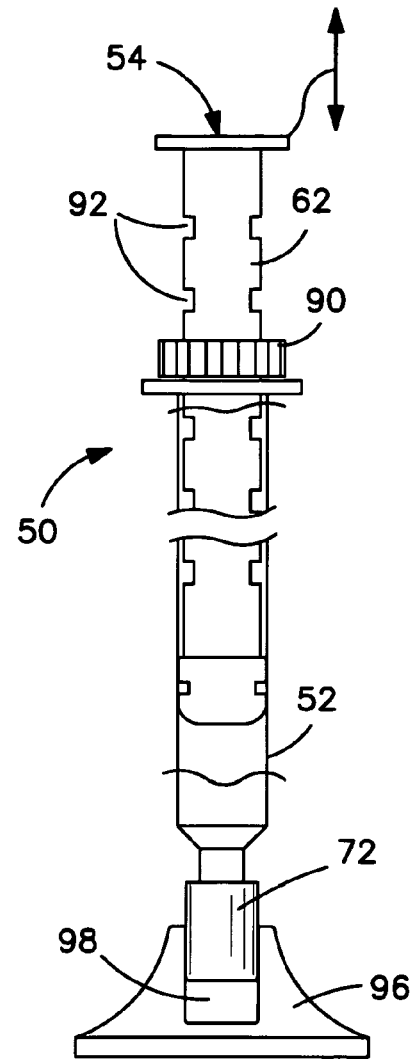
FIG. 3 shows the dispensing syringe fitted to a support base and provided with a unit dose dial for dispensing a unit dose amount from a multiple-dose medicament container.

Referring again to FIG. 3, a system for dispensing mixtures is provided with an optional support base 96 having an interior opening 98 that receives cap 72. Thus, with a single hand available, an operator can conveniently insert dispensing syringe 50 in a temporary position that seals the opening of the dispensing syringe, shielding its free end against contamination caused by inadvertent contact with the dispensing orifice 54 and free end 56 of dispensing syringe 50 (see FIG. 2).

While the mixing devices and dispensing syringes may be made to virtually any dimension desired, representative examples of typical applications can be given. For example, in one embodiment, the mixing chamber, when adapted to an emulsification operation, preferably has one or more emulsification channels or pathways having an internal diameter of about 0.01 to about 0.05 inches, and more preferably are in the range of about 0.02 to about 0.04 inches.

The syringe component of mixing device 10, that is, tubular housing 14 and plunger 46, are preferably dimensioned so as to hold about 1 milliliter (ml) of the formulation. In one example, tubular housing 14 has an internal diameter ranging about 0.3 to about 0.7 inches and more preferably about 0.5 to about 0.6 inches. For multiple milliliter size dose capacity, the ranges for the tubular housing are multiplied by the number of milliliters of dose desired. For example, for an x milliliter formulation content, the internal diameter of tubular housing 14 ranges about 0.3x to about 0.7x inches, and more preferably about 0.5x to about 0.6x inches.

A relatively large ratio of internal diameter of tubular housing 14 with respect to the internal diameters of the emulsification channels in the mixing chamber makes the mixing of the two components more efficient. Preferably the ratio of the internal diameter of tubular housing 14 to the internal diameter of a emulsification channel is at least about 6:1, more preferable, in the range of about 15:1 to about 30:1.

For a dispensing syringe holding a 1 ml of formulation, the internal diameter of the tubular housing 52 preferably ranges between 0.3 and 0.7 inches, most preferably between 0.3 and 0.4 inches. For multiple milliliter capacity, a formulation content of x ml is accommodated by tubular housing 52 having an internal diameter ranging between 0.3x and 0.7x inches, and most preferably between 0.3× and 0.4× inches. A relatively small internal diameter for the dispensing syringe (with an extended length) improves the accuracy of dispensing of the resultant mixture.

As will be appreciated, a number of advantages are provided by the present invention, over emulsification needles and similar devices. For example, whereas prior art emulsification needles provide a single mixing channel, the present invention provides one or more mixing channels to increase mixing efficiency, thereby reducing the number of iterations or passes through the mixing chamber. Further, with multiple mixing channels, pumping resistance from high viscosity formulations is effectively reduced.

By configuring the mixing chamber with a tubular housing forming a first syringe, separation of mixing chamber and a first syringe is eliminated. This is an important feature when elevated pumping pressures are associated with a mixing event. Whereas emulsifying needles employed a plug-in engagement, the present invention provides a secure interlock between the mixing device and the second dispensing syringe to prevent unintentional separation, especially during mixing events having elevated pumping pressures.

As an additional advantage, the emulsifying needles employed heretofore are, for reasons of economy, adapted for use with general purpose syringes having standard interfitting features. While attractive from the point of view of cost savings, general purpose syringes may be made from a variety of materials, some of which are unsuitable for a particular application. For example, the resilient plungers fitted to many disposable syringes may be made of an elastomeric material that is incompatible or otherwise unsuitable for use with certain mixture components. With the present invention, economical disposable mixing devices and dispensing plungers are provided that are readily adaptable for use with special purpose applications, thereby ensuring materials compatibility throughout a mixing and dispensing system.

As an additional advantage, whereas emulsifying needles are adapted for reuse without regard to the particular components involved, mixing devices and dispensing syringes according to principles of the present invention can be made from specially selected materials and may be color coded for different materials. Alternatively, the free end of the dispensing syringe may be keyed with a particular shape that can be mated only with mixing devices having a complementary key shape, to ensure that the two are suitable for use, one with the other.

The foregoing description and the accompanying drawings are illustrative of the present invention. Still are the variations in arrangements of parts are possible without departing from the spirit and scope of this invention.

We claim:

1. A syringe comprising:
    a generally tubular housing having opposing proximal and distal end portions, the distal end portion terminating in a nozzle defining a mixing chamber, wherein the tubular housing and mixing chamber are a unitary molded body; and
    a plunger configured for axial movement with the tubular housing wherein the mixing chamber includes at least one emulsifying passageway formed by an internal structure disposed within the mixing chamber and wherein the interior structure has opposed ends that are flared in an inwardly extending or concave frustoconical shape.

2. The syringe in accordance with claim 1 wherein the mixing chamber is adapted to interlock with an external device to receive a liquid infusion through the mixing chamber.

3. The syringe in accordance with claim 1 wherein the mixing chamber includes a plurality of emulsifying passageways.

4. A system for mixing and dispensing, comprising:
    a mixing device including a generally tubular housing having opposing proximal and distal end portions, the distal end portion terminating in a nozzle located adjacent a mixing chamber, wherein the tubular housing and mixing chamber are a unitary molded body;
    the mixing device further including a plunger configured for axial movement within the tubular housing to displace material disposed therein through the mixing chamber and the nozzle, wherein the mixing chamber includes at least one emulsifying passageway formed by an internal structure disposed within the mixing chamber; wherein the interior structure has opposed ends that are flared in an inwardly extending or concave frustoconical shape; and
    a dispensing syringe having a syringe housing terminating in a free end adapted to interfit with the nozzle.

5. The system in accordance with claim 4 wherein the nozzle is adapted to interlock with the free end of the dispensing syringe.

6. The system in accordance with claim 4 wherein the mixing chamber includes a plurality of emulsifying passageways.

\* \* \* \* \*